United States Patent
Heesch

(10) Patent No.: US 7,987,849 B2
(45) Date of Patent: Aug. 2, 2011

(54) METHOD FOR DETERMINING THE CONSUMPTION OF A $CO_2$ ABSORBER IN A RESPIRATOR WITH REBREATHING SYSTEM

(75) Inventor: Ralf Heesch, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1034 days.

(21) Appl. No.: 11/832,913

(22) Filed: Aug. 2, 2007

(65) Prior Publication Data

US 2008/0105260 A1 May 8, 2008

(30) Foreign Application Priority Data

Nov. 2, 2006 (DE) .................. 10 2006 051 571

(51) Int. Cl.
*A62B 7/10* (2006.01)
*B01D 53/14* (2006.01)

(52) U.S. Cl. ......... 128/205.28; 128/204.18; 128/205.12; 128/205.27; 95/139

(58) Field of Classification Search ............... 128/20.24, 128/201.25, 202.22, 204.18, 204.21, 204.22, 128/205.12, 205.23, 205.27, 205.28; 95/1, 95/12, 139; 96/108
See application file for complete search history.

(56) References Cited

U.S. PATENT DOCUMENTS

| | | | | |
|---|---|---|---|---|
| 4,233,842 A * | 11/1980 | Raemer et al. | ............. | 73/861.04 |
| 4,440,162 A * | 4/1984 | Sewell et al. | ............. | 128/202.22 |
| 4,856,531 A * | 8/1989 | Merilainen | ............. | 600/532 |
| 4,917,108 A * | 4/1990 | Mault | ............. | 600/531 |
| 5,120,511 A * | 6/1992 | Luft | ............. | 422/86 |
| 5,694,924 A * | 12/1997 | Cewers | ............. | 128/204.21 |
| 5,806,513 A * | 9/1998 | Tham et al. | ............. | 128/204.22 |
| 6,009,871 A * | 1/2000 | Kiske et al. | ............. | 128/204.21 |
| 6,035,851 A * | 3/2000 | Wallen | ............. | 128/202.22 |
| 6,162,281 A * | 12/2000 | Ammann et al. | ............. | 95/8 |
| 6,537,347 B2 * | 3/2003 | Motouji et al. | ............. | 95/8 |
| 6,629,933 B1 * | 10/2003 | Lindner | ............. | 600/532 |
| 7,089,930 B2 * | 8/2006 | Adams et al. | ............. | 128/201.27 |
| 7,148,806 B2 * | 12/2006 | Anttila et al. | ............. | 340/573.1 |
| 7,669,594 B2 * | 3/2010 | Downie | ............. | 128/203.12 |
| 2002/0023643 A1 * | 2/2002 | Hoffmann | ............. | 128/203.12 |
| 2002/0023646 A1 | 2/2002 | Heesch | | |
| 2003/0074154 A1 | 4/2003 | Warkander | | |
| 2005/0217671 A1 * | 10/2005 | Fisher et al. | ............. | 128/204.18 |

* cited by examiner

*Primary Examiner* — Justine R Yu
*Assistant Examiner* — LaToya M Louis
(74) *Attorney, Agent, or Firm* — McGlew and Tuttle, P.C.

(57) ABSTRACT

A method for determining the consumption of a $CO_2$ absorber (8) in a respirator with a rebreathing system, with a fresh gas mixer (1) and with a computing and control unit (10). The rebreathing system has a respiration drive (2), a volume flow sensor (3) located in the inspiratory branch, a $CO_2$ absorber (8) located in the expiratory branch, whose output, combined with that of the fresh gas mixer (1), is fed into the inspiratory branch, a breathing gas escape valve (7) and a breathing gas reservoir (9). The computing and control unit (10) is connected to the fresh gas mixer (1), to the respiration drive (2) and to the volume flow sensor (3) in order to receive signals and send control commands. The fresh gas volume flow $V_{FG}$ discharged from the fresh gas mixer (1) and the inspiration volume flow $V_I$ flowing into the inspiratory branch are determined in the method in the computing and control unit (10). A value for the purified rebreathing volume flow $V_{abs}$ admitted from the $CO_2$ absorber (8) is determined from the difference $V_I - V_{FG}$ of those values, and a rate of $CO_2$ absorption is determined herefrom on the basis of a preset $CO_2$ concentration value or from a $CO_2$ concentration value measured with a gas sensor in the expiratory branch and integrated over time in order to determine the quantity of $CO_2$ absorbed in the $CO_2$ absorber (8).

20 Claims, 2 Drawing Sheets

METHOD FOR DETERMINING THE CONSUMPTION OF A CO₂ ABSORBER IN A RESPIRATOR WITH REBREATHING SYSTEM

CROSS REFERENCE TO RELATED APPLICATIONS

This application claims the benefit of priority under 35 U.S.C. §119 of German Patent Application DE 10 2006 051 571.4 filed Nov. 2, 2006, the entire contents of which are incorporated herein by reference.

FIELD OF THE INVENTION

The present invention pertains to a method for determining the consumption of a carbon dioxide ($CO_2$) absorber in a respirator (ventilator) with rebreathing system.

BACKGROUND OF THE INVENTION

Such a respirator has a fresh gas mixer, which provides the breathing gas mixture, a control unit and a rebreathing system. The rebreathing system has a respiration drive, e.g., a fan or a radial compressor, a volume flow sensor located in the inspiratory branch, a $CO_2$ absorber located in the expiratory branch, whose output, combined with that of the fresh gas mixture, is fed again into the inspiratory branch, where a breathing gas escape valve for drawing off excess breathing gas when a pressure limit is reached, and a breathing gas reservoir are connected, mostly in the expiratory branch. The control unit controls the fresh gas mixer and the respiration drive and receives signals from sensors, e.g., from the inspiratory volume flow sensor.

When the expired gas is again returned into the inspiratory branch in such a system, the $CO_2$ must be removed from the expired breathing gas, which is done by means of a $CO_2$ absorber. Breathing lime is typically used as the absorber material in such a $CO_2$ absorber. The gas expired by the patient flows through the breathing lime present in the $CO_2$ absorber. The $CO_2$ present in the breathing gas is now absorbed by the breathing lime and is thus removed from the gas flow. The breathing lime is depleted after a total quantity of $CO_2$ absorbed, which depends on the quantity of breathing lime, and no more $CO_2$ can be absorbed any longer. The expired $CO_2$ would again be introduced into the patient during inspiration, after which correct breathing would not be guaranteed any longer.

The consumption of breathing lime can be recognized from the change in color of the breathing lime, which is associated with the depletion of the breathing lime. However, since it is undesirable, as a rule, to have to replace the breathing lime in the $CO_2$ absorber or the entire $CO_2$ absorber during an operation, it would be very useful if the staff could be provided with information on the state of consumption of the $CO_2$ absorber.

A reliable and accurate calculation of the quantity of $CO_2$ absorber absorbed by the $CO_2$ absorber is not performed in the respirators currently available commercially. Thus, measurement/monitoring of the degree of depletion of the $CO_2$ absorber is not yet possible in practice. An anesthesiologist can therefore use only the change in color of the breathing lime as an indicator for the necessary replacement of the breathing lime. Therefore, it often happens that there is a response only when the $CO_2$ content measured by a connected monitoring unit in the inspiratory air of the patient to be respirated is above preset limit values and corresponding alarms, derived herefrom, warn the operating staff.

SUMMARY OF THE INVENTION

The object of the present invention is to provide a method with which the cumulative quantity of absorbed $CO_2$ in a $CO_2$ absorber can be reliably determined, especially without the need for additional sensors of instruments other than those usually already present in the respiration system.

A method is provided for determining the consumption of a $CO_2$ absorber in a respirator with a rebreathing system. The rebreathing system has a fresh gas mixer, a computing and control unit, a respiration drive, a volume flow sensor located in the inspiratory branch, a $CO_2$ absorber, which is located in the expiratory branch and whose output, combined with that of the fresh gas mixer, is sent to the inspiratory branch, a breathing gas escape valve and a breathing gas reservoir. The computing and control unit is connected to the fresh gas mixer, the respiration drive and the volume flow sensor to receive signals and to send control commands. The fresh gas volumes discharged from the fresh gas mixer and the inspiration volume flow flowing into the inspiratory branch are determined according to the method in the computing and control unit. A value for the purified rebreathing volume flow added from the $CO_2$ absorber is determined from the difference of those values, and a rate of $CO_2$ absorption is determined and integrated over time from this on the basis of a preset $CO_2$ concentration value or a $CO_2$ concentration value measured with a gas sensor in the expiratory branch in order to determine the quantity of the $CO_2$ absorbed in the $CO_2$ absorber.

The present invention is based on determining the balance of the volume flows in the respiration system as accurately as possible in order to determine the quantity of $CO_2$-containing expired gas, which has flown through the $CO_2$ absorber, as accurately as possible, in order to determine from this the quantity of absorbed $CO_2$ by means of a value of the $CO_2$ concentration in the expired breathing gas.

To determine the balance of the volume flows through the $CO_2$ absorber, the fresh gas volume flow and the inspiration volume flow flowing in the inspiratory branch are determined. Since the inspiration volume flow is composed of the fresh gas volume flow and the purified breathing gas added from the $CO_2$ absorber volume flow, a value can be determined on the basis of the difference between the inspiratory volume flow and the fresh gas volume flow for the purified rebreathing volume flow added from the $CO_2$ absorber, the added volume flow being determined according to the general aspect of the present invention by integrating the positive components of $V_i - V_{FG}$, i.e., negative refluxes to the absorber remain ignored in the general embodiment.

The quantity of $CO_2$ absorbed in the $CO_2$ absorber can be calculated by means of the volume flow discharged from the $CO_2$ absorber and the $CO_2$ concentration in front (upstream) of the absorber. The absorbed $CO_2$ concentration of the absorber is approximately equal to the product of the volume flow from the absorber and the $CO_2$ concentration in front of the absorber. However, a more accurate calculation is preferably carried out, in which the volume flow reduction in the $CO_2$ absorber due to the absorption of $CO_2$ is taken into account and the volume flow $V^{in}_{abs}$ entering the $CO_2$ absorber is calculated; this can be carried out by means of the equation:

$$\dot{V}^{in}_{abs} = \dot{V}_{abs}\left(\frac{100}{100 - Vol. \% (CO_2)}\right)$$

At a $CO_2$ content of 5 vol. %, this means that the volume flow in front of the $CO_2$ absorber is 100/95=1.053 times greater than the observed volume flow behind (downstream of) the $CO_2$ absorber. The product of this volume flow $\dot{V}^{in}_{abs}$ entering the $CO_2$ absorber and the $CO_2$ concentration in front of the absorber yields the quantity of $CO_2$ absorbed in the absorber per unit of time.

The above-described procedure for determining the quantity of absorbed $CO_2$ basically somewhat overestimates the actual quantity because it is not taken into account that $CO_2$-free gas can flow through the $CO_2$ absorber against the direction of the expired breathing gas during certain phases, so that a $CO_2$-free volume can form in front of the $CO_2$ absorber, and this volume will first flow through the absorber and contribute to the volume flow from the $CO_2$ absorber only during the next expiration phase, without, however, depositing $CO_2$ in the absorber. This happens especially when operating with a continuous fresh gas volume flow. No inspiratory volume flow is flowing at times outside the inspiration phase, so that the fresh gas flowing in continuously in the opposite direction flows through the $CO_2$ absorber and further through the line up to an anesthetic gas escape valve. This entire volume in front of the $CO_2$ absorber up to the anesthetic gas escape valve can consequently be filled with $CO_2$-free gas, which is pushed through the $CO_2$ absorber first during the next inspiration cycle. This maximum $CO_2$-free volume will hereinafter also be called buffer volume. It must be determined and stored in advance for each rebreathing system depending on the design, dimensions and line connections of this rebreathing system. During phases during which the volume flow $V_{FG}$ from the fresh gas mixer is greater than the inspiratory flow $V_i$, fresh gas flowing off in the direction of the $CO_2$ absorber is preferably balanced as a $CO_2$-free volume in front of the $CO_2$ absorber by integrating the volume flow $(V_{FG}-V_i)$ flowing through the $CO_2$ absorber up to the preset maximum buffer volume and storing it as a $CO_2$-free volume value, and the $CO_2$-free volume flow is subtracted from the integrated volume flow through the absorber during the next inspiration phase, when the inspiratory volume flow $V_i$ is greater than the fresh gas volume flow $V_{FG}$.

The control unit is preferably set up in the method to receive and store the maximum quantity of absorbed $CO_2$ which the $CO_2$ absorber can absorb and/or to initiate the sending of an audio signal upon input by an operator, as soon as the integrated quantity of absorbed $CO_2$ exceeds the stored maximum.

The present invention will be described below on the basis of an exemplary embodiment in connection with the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
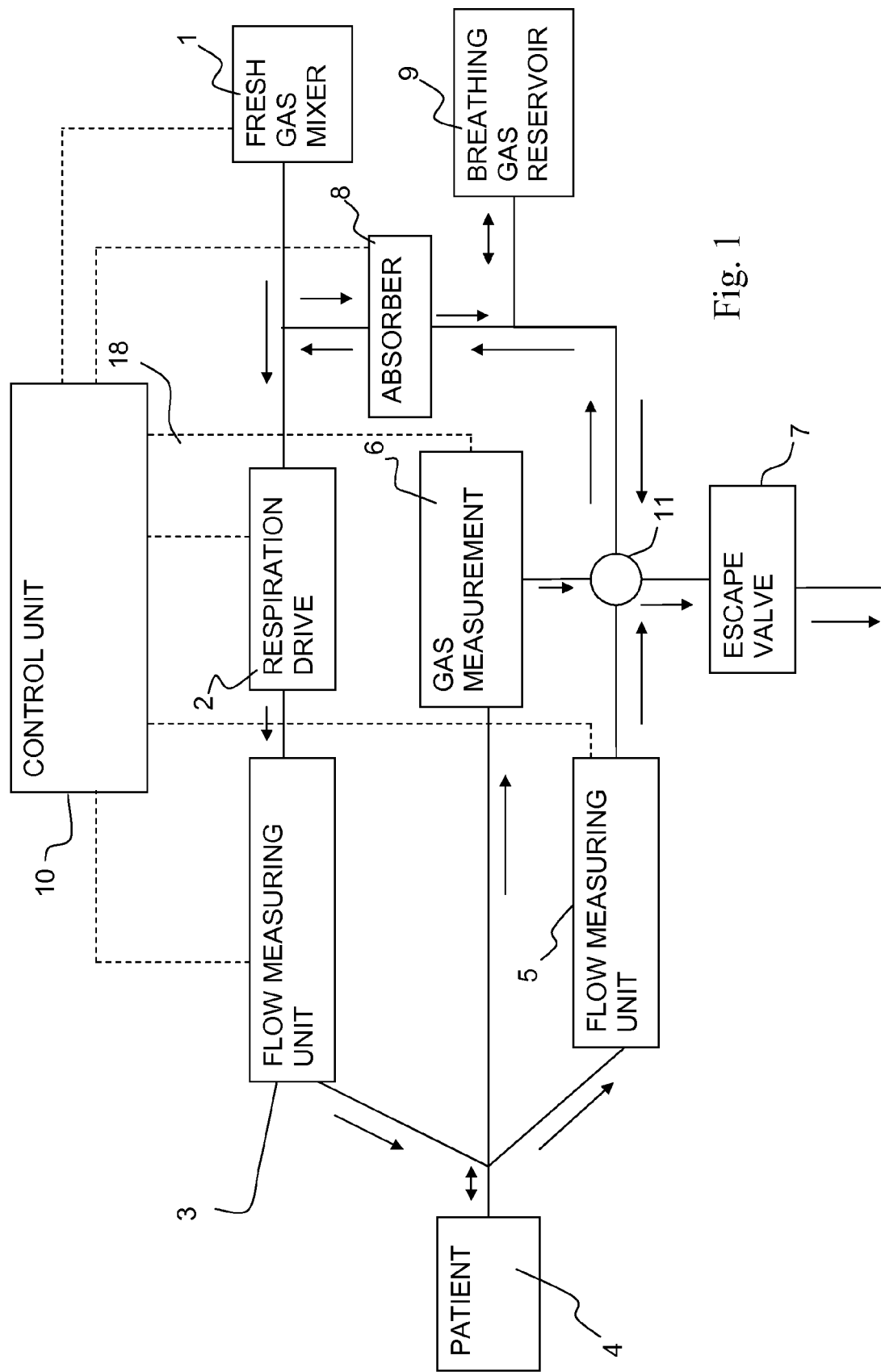
FIG. 1 is a schematic view showing the design of a rebreathing system for use with the present invention.

Referring to the drawings in particular, FIG. 1 shows as an example the schematic design of a rebreathing system suitable for the application of the present invention. The arrows indicate the direction of a gas flow to and from an element. The valves guaranteeing the direction of gas flow are not shown here because these are irrelevant for the principle of determining the $CO_2$ absorber consumption being described here, only the directions of the particular gas flows being relevant. Broken lines without an indicated direction indicate an electric connection or a data communications section, along which information is transported from elements of the rebreathing system to a central computing and control unit 10 or also the other way around.

A gas mixture (usually composed of the individual gases $O_2$, air, $N_2O$, volatile anesthetic gases) are sent in the fresh gas mixer to the rebreathing system corresponding to the setting made by the user or the operator. This gas flow is usually called "fresh gas." The volume of the fresh gas volume flow is reported back to the computing and control unit 10. The fresh gas mixer 1 may be a mechanical mixer, which is equipped with an electronic gas volume flow measurement, or also an electronic mixer, which receives the metering data from the computing and control unit 10.

On the way to the respiration drive, the fresh gas is mixed with the volume expired during the expiration, which originates from the patient 4 and is freed of $CO_2$ in the $CO_2$ absorber, and is delivered to the patient 4 through the (inspiratory) volume flow measuring unit 3 in the respiration drive in a volume- and/or pressure-controlled manner. The (inspiratory) volume flow measuring unit 3 sends the volume flow information $V_i$ measured in the method to the computing and control unit 10.

After the inspiration phase, the patient 4 can again release an expired expiration volume to the rebreathing system through the (expiratory) volume flow measuring unit 5. The (expiratory) volume flow measuring unit 5 sends the volume flow information measured in the process to the computing and control unit 10.

The expiratory volume flow expired by the patient is split into different branches within the rebreathing system. One part is admitted into the breathing gas reservoir 9 (this may be identical to parts of the respiration drive in other systems), from which it is then available at the beginning of the next inspiration phase for the respiration drive 2, flowing through the $CO_2$ absorber 8.

Another part of the expired breathing gas is fed to an anesthetic gas escape through the anesthetic gas escape valve 7. The anesthetic gas escape valve 7 opens only beginning from a defined internal pressure in the system, so that the breathing gas reservoir 9 must first be filled completely before anesthetic gas is lost from the system.

The gas concentrations ($O_2$, $CO_2$, $N_2O$, volatile anesthetic gases) are measured during the breathing (respiration) at the point at which the inspiratory and expiratory connection of the rebreathing system is connected to the patient 4 (the so-called "Y-piece"). This may be carried out by a so-called suctioning (sidestream) gas measurement or also a directly measuring gas measurement integrated in or connected to the Y-piece. This is shown in FIG. 1 by the suctioning gas measurement, which feeds the gas flow drawn off to the rebreathing system.

The proportional breathing lime consumption is determined, on the one hand, by the user setting the maximum quantity of $CO_2$ to be absorbed per absorber filling in a configuration menu on the computing and control unit 10 and, on the other hand, by a volume flow balancing, by which the $CO_2$ volume absorbed in the $CO_2$ absorber 8 is determined.

The user or the operator must likewise communicate for this to the system (e.g., by manual acknowledgment on the computing and control system 10) when the breathing lime in the $CO_2$ absorber 8 (or the $CO_2$ absorber 8 as a whole) was changed. If only a certain $CO_2$ absorber 8 with, e.g., a defined, preset breathing lime can be used or is released for the particular rebreathing system, the limit of the maximum volume of $CO_2$ to be absorbed by this $CO_2$ absorber may likewise be preset by the manufacturer of the entire system already at the time of the sale of the device (e.g., in the computing and control unit 10).

At another level of expansion, $CO_2$ absorbers 8 may be provided, e.g., with radio frequency identification (RFID) tags, so that an electronic unit integrated in the control and computing unit 10 (or connected thereto externally) automatically recognizes the replacement of the $CO_2$ absorber 8; the manual acknowledgement of the replacement of the breathing lime, which is otherwise necessary on the part of the user, would thus become unnecessary.

The calculation of the $CO_2$ volume absorbed by the $CO_2$ absorber 8 is then restarted at a value of "0" after the breathing lime replacement announced by the computing and control unit 10 and continued/integrated until the next absorber replacement (also beyond the switching on and off of the device).

The calculation of the total volume of $CO_2$ absorbed by the $CO_2$ absorber 8 is carried out primarily on the basis of the inspiratory volume flow $V_I$, which is measured by means of the inspiratory volume flow measuring unit 3 or is derived from the setting of the respiration drive 2, which setting is known to the control unit, and the fresh gas volume flow $V_{FG}$ (through the fresh gas mixer 1, which is known to the computing and control unit 10). Any volume that is fed to the patient during the inspiration phase must consist of the addition of the volume taken from the fresh gas mixer 1 and the $CO_2$ absorber 8.

The quantity of (patient) gas previously enriched with $CO_2$ that has flown through the $CO_2$ absorber 8 is thus known, in principle: $V_{abs}=V_I-V_{FG}$. The percentage of $CO_2$ in the air expired by the patient can be determined by means of the gas measurement 6, so that the percentage of the $CO_2$ volume reacted in the $CO_2$ absorber can be determined by means of this $CO_2$ concentration and the total volume (determined according to the above) that has flown through the $CO_2$ absorber.

As an alternative (resulting in higher inaccuracy), the gas measurement may also be eliminated because the $CO_2$ value of respirated patients is only in a relatively narrow possible range during average respiration. The value of the $CO_2$ concentration, which is to be taken into account, can thus be preset as a fixed value or it may also be configured by the user.

The inspiratory volume flow fed to the patient during inspiration can also be replaced or supplemented with information from the respiration drive 2 instead of information from an inspiratory volume flow measurement 3.

If the fresh gas volume flow is fed by the fresh gas mixer 1 to the rebreathing system continuously, it should also be taken into account (also as a function of the position of the manual respiration bag 9 present in the rebreathing system), to increase the accuracy of the algorithm, that a volume flow is flowing through the $CO_2$ absorber 8 in the direction of the anesthetic gas escape valve 7 during the patient's "non-inspiration phase."

The volume between the $CO_2$ absorber 8 and the anesthetic gas escape valve 7 is thus replaced by $CO_2$-free air. The $CO_2$ absorber 8 does not have to free this component of the $CO_2$-free volume of $CO_2$ at the beginning of the next inspiration phase, so that this volume percentage is subtracted from the reacted $CO_2$ volume (determined according to the above without this correction) in a preferred embodiment.

This shows clearly that the design of the particular rebreathing system being considered must be taken into account when forming the model for the determination of the $CO_2$ volume absorbed by the $CO_2$ absorber, because the total volume between the $CO_2$ absorber 8 and the anesthetic gas escape valve 7 depends on the line volumes of the particular rebreathing system and must be determined and stored in advance, because it sets the maximum buffer volume with $CO_2$-free gas in front of the $CO_2$ absorber 8.

Figure 2:
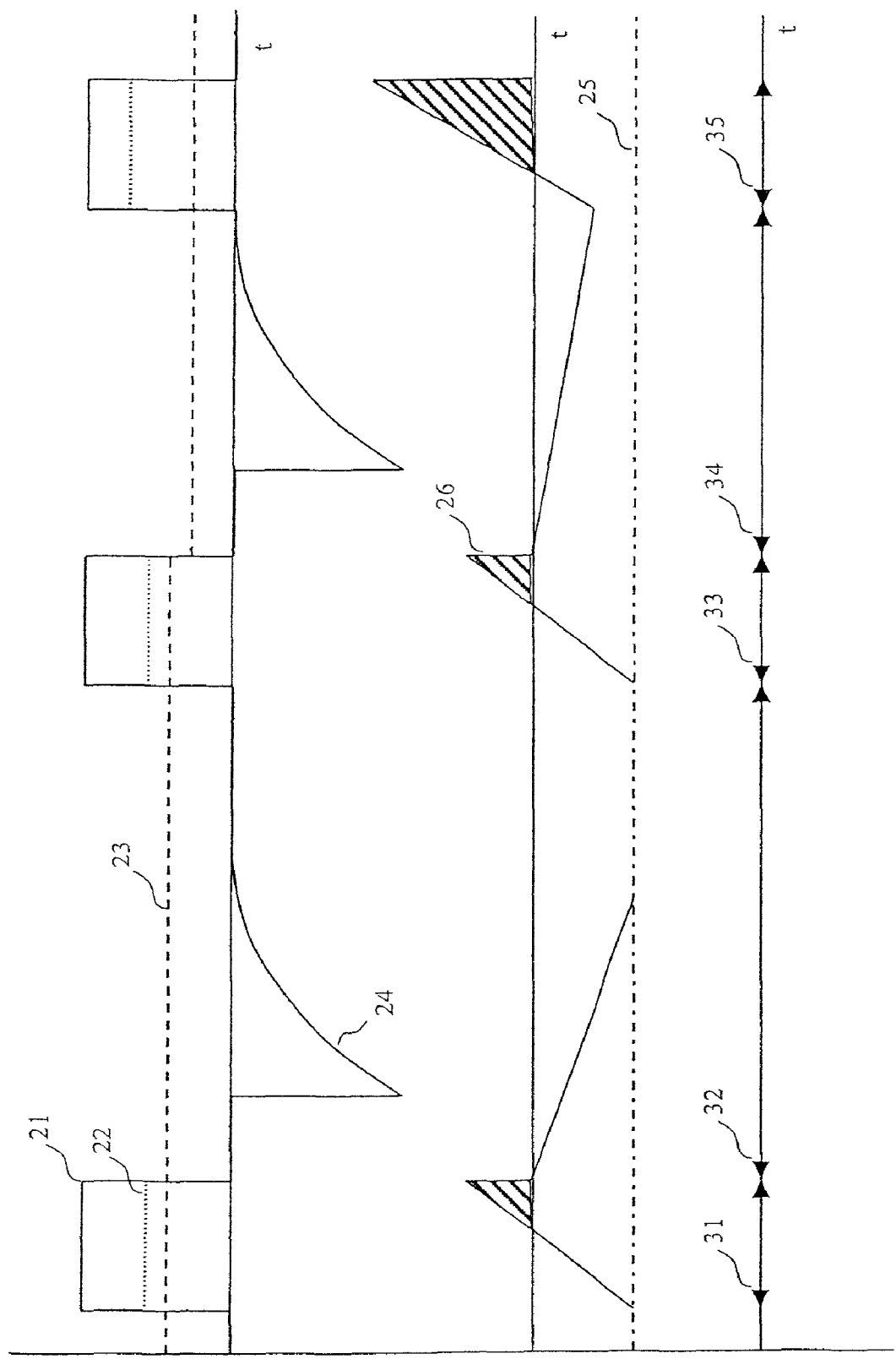
FIG. 2 is a graph with the volume flows and the volume passing through the $CO_2$ absorber as a function of time.

The calculation shall be explained in more detail in FIG. 2 on the basis of the rebreathing system outlined schematically in FIG. 1. The volume flow to and from the manual respiration bag is ignored here, because this can be minimized by other measures (see DE 100 41 007 C1); the percentage of $CO_2$ expired by the patient is likewise assumed to be constant in this illustration.

The volume flows that are relevant for this calculation in the system are plotted on the upper curve. The volume flows flowing to the patient are assumed to be constant here for illustration (e.g., during respiration with constant volume), and they are represented by the inspiration volume flow $V_I$ 21. The expiration volume flow is designated by 24. The fresh gas volume flow $V_{FG}$ supplied by the fresh gas mixer 1 is designated by 23.

The calculated volume ratios for the $CO_2$ absorber 8 are plotted on the middle curve. If a volume flow containing $CO_2$ is delivered through the $CO_2$ absorber, a $CO_2$ volume is integrated (positive range of the $CO_2$ volume curve 26, illustrated as an area drawn by broken lines under the $CO_2$ volume curve 26). The negative range of curve 26 designates the current $CO_2$-free volume in the buffer volume between the $CO_2$ absorber 8 and the intersection 11.

The phases of the respiration cycles just described are shown on the lower curve. The inspiration volume flows 21 are equal and of equal duration in all three inspiration phases (31, 33, 35) shown. This results in a total inspiration volume which is equal for each breathing stroke.

Phase 31 (Inspiration):

The fresh gas volume flow 23 is relatively high, and only a certain volume flow 22 must therefore be delivered through the $CO_2$ absorber 8.

The starting condition assumed in this calculation is that the volume between the absorber 8 and the intersection 11 is completely free of $CO_2$ before this first breathing stroke. This volume is called the maximum buffer volume 25 here.

If volume is now delivered through the $CO_2$ absorber 8 in the direction of the patient, $CO_2$-free gas will first flow through the $CO_2$ absorber 8 (corresponding to the size of the maximum buffer volume), represented by a rise of curve 26. If the volume flowing through the $CO_2$ absorber 8 is greater than the $CO_2$-free volume present in the buffer volume, $CO_2$-containing gas will be delivered from the (preceding) expiration phase through the $CO_2$ absorber 8 and absorbed in the $CO_2$ absorber 8. As a result, the remaining absorption capacity of the $CO_2$ absorber 8 is correspondingly reduced. The $CO_2$ content in the expiration air of the preceding expiration phase is decisive here. The fact that the volume of $CO_2$-containing air decreases on its way through the $CO_2$ absorber 8 because the $CO_2$ is extracted may likewise be taken into account in the calculation. This means that the volume of $CO_2$-containing air entering the $CO_2$ absorber 8 must be larger than the volume of $CO_2$-free air that is discharged and the percentage of absorbed $CO_2$ volume is thus correspondingly increased.

Phase 32 (Expiration):

After the end of the flow phase during the inspiration, the continuously flowing gas volume flow 23 is not delivered to the patient any longer, i.e., it must be sent through the absorber 8 in the direction of the anesthetic gas escape valve 7. The buffer volume is flushed with $CO_2$-free air now. The $CO_2$-free volume, which is thus present in the buffer volume until the inspiration phase begins the next time, depends on the fresh gas volume flow 23 set and the time available until the next inspiration phase. However, the maximum volume is limited here by the space present in the respiration system due to the design between the $CO_2$ absorber 8 and the intersection 11, represented as a maximum buffer volume 25 here. The maximum buffer volume of $CO_2$-containing air is purified during phase 32 (due to the relatively high setting of the fresh gas volume flow 23 and the long time of this phase).

Phase 33 (Inspiration):
This phase is identical to phase 31 here.
Phase 34 (Expiration):
The fresh gas volume flow 23 is reduced at the beginning of this phase. The buffer volume is thus freed of $CO_2$ to a lesser extent only compared to what happened in phase 32; the maximum buffer volume is not utilized in this case.
Phase 35 (Inspiration):
A certain percentage of $CO_2$-free gas is delivered through the $CO_2$ absorber 8 here as well, but less than in the preceding phase 33, because the $CO_2$ absorber-free volume buffered was smaller. Therefore, more $CO_2$-free gas is delivered through the $CO_2$ absorber 8. In addition, because the fresh gas volume flow 23 was reduced, a larger volume must be delivered through the $CO_2$ absorber 8; this can be recognized from a sharper rise of curve 26 compared to phase 33. Both lead to the circumstance that a considerably larger volume of $CO_2$ must be absorbed in the $CO_2$ absorber 8 in phase 35 than in phases 31 and 33.

The $CO_2$ volumes thus determined for individual breathing strokes can then be integrated and thus they represent the quantity of $CO_2$ absorbed by the $CO_2$ absorber 8.

If the maximum quantity of $CO_2$ absorbed, which was set by the user or the operator on the computing and control unit 10, has been reached or exceeded, the entire device can inform the person setting up the entire device visually and/or audibly that the maximum $CO_2$ absorption capacity of the connected $CO_2$ absorber 8 is exceeded and the latter (or the breathing lime therein) must therefore be replaced. Otherwise, e.g., the still remaining residual capacity of the breathing lime may be displayed to the user.

In addition, the user or the operator may possibly also set on the computing and control unit 10 by how much sooner than the set maximum absorption capacity of the breathing lime the reports shall occur during the setting up (and/or during the later operation of the entire device). The user can then determine whether warning should be given rather early (=meaning maximum safety for the patient) or rather late (=meaning maximum utilization of the breathing lime).

The residual capacity of the breathing lime may be displayed, e.g., as a percentage value (expressing the ratio of the $CO_2$ volume already absorbed to the maximum limit set by the user), as a still remaining value of $CO_2$ volume that can still be absorbed (indicating the quantity, e.g., in liters), or also as a still remaining residual time of the $CO_2$ absorber. If the residual time is indicated, the underlying algorithm as the basis of the time indication can calculate, e.g., the time within which (during ongoing respiration) a certain volume of $CO_2$ was absorbed by the $CO_2$ absorber 8 in the past of the entire device (based on the assumption that the user/the entire device will continue to behave comparably concerning the $CO_2$ absorption characteristic in the $CO_2$ absorber as in the past in case of similar settings).

If necessary, the user or the operator may also be provided with the warnings described above during the ongoing operation of the device in the form of, e.g., visual/audible alarm reports.

Furthermore, the date of the first use of this particular $CO_2$ absorber 8 can be written, e.g., on the RFID tag in the case of a $CO_2$ absorber 8 equipped with, e.g., an RFID tag. If a $CO_2$ absorber 8, which already has a set date on the RFID tag, is then connected to a rebreathing system, the computing and control unit can visually and/or audibly warn the user that a $CO_2$ absorber that had already been used was connected to the particular entire device.

The information that the $CO_2$ absorber 8 has already been used can be written, e.g., on an RFID tag with indication of the date of the first use or also as a simple flag or also in any other form (and it can then be read by the computing and control unit 10).

If the date of first use is written on, e.g., the RFID tag of the $CO_2$ absorber 8, the date thus stated can be used, furthermore, e.g., to inform the person performing the set-up, e.g., during the setting up of the entire device, visually and/or audibly that, e.g., a maximum use time of the connected $CO_2$ absorber 8, which is to be set, e.g., by the user on the computing and control unit 10, and after which the $CO_2$ absorber 8 shall be replaced (e.g., for hygienic reasons) at the latest, has been exceeded. If necessary, this warning may also be provided for the user during the ongoing operation of the device in the form of, e.g., visual/audible alarm reports.

While a specific embodiment of the invention has been shown and described in detail to illustrate the application of the principles of the invention, it will be understood that the invention may be embodied otherwise without departing from such principles.

What is claimed is:

1. A method for determining the consumption of a $CO_2$ absorber in a respirator with a rebreathing system, the method comprising the steps of:

providing the rebreathing system with a fresh gas mixer, with a computing and control unit, a respiration drive, a volume flow sensor located in an inspiratory branch, a $CO_2$ absorber located in an expiratory branch, the $CO_2$ absorber providing an output that is combined with an output of said fresh gas mixer and is sent to said inspiratory branch, a breathing gas escape valve and a breathing gas reservoir;

connecting said computing and control unit to said fresh gas mixer, to said respiration drive and to said volume flow sensor to receive signals at said computing and control unit and to send control commands from said computing and control unit to said fresh gas mixer and to said respiration drive;

determining a fresh gas volume ($V_{FG}$) discharged from said fresh gas mixer and inspiration volume flow ($V_I$) flowing into the inspiratory branch in said computing and control unit;

determining a value for a purified rebreathing volume flow ($V_{abs}$) added from said $CO_2$ absorber from a difference of the values of the inspiration volume flow and the fresh gas volume ($V_I$-$V_{FG}$) and determining a volume flow entering the $CO_2$ absorber from the value for the purified rebreathing volume flow and a preset or sensed $CO_2$ concentration value of gas flowing into the $CO_2$ absorber;

determining a rate of $CO_2$ absorption from the volume flow entering the $CO_2$ absorber and from the preset or sensed $CO_2$ concentration value;

integrating the determined rate of $CO_2$ absorption over time on the basis of the preset $CO_2$ concentration value or the sensed $CO_2$ concentration value measured with a gas sensor in the expiratory branch in order to determine the quantity of the $CO_2$ absorbed in said $CO_2$ absorber.

2. A method in accordance with claim 1, further comprising performing a correction, which takes into account the fact that said volume flow ($V_{abs}$) discharged from said $CO_2$ absorber is smaller than a volume flow entering said $CO_2$ absorber because of the $CO_2$ absorption in said $CO_2$ absorber, during the calculation of the rate of $CO_2$ absorption on the basis of said volume flow ($V_{abs}$) discharged from said $CO_2$ absorber and the $CO_2$ concentration.

3. A method in accordance with claim 1, further comprising: balancing fresh gas flowing off in the direction of said $CO_2$ absorber which is $CO_2$-free volume upstream of said $CO_2$ absorber, during continuous inflow of fresh gas from said fresh gas mixer during phases during which said volume flow from said fresh gas mixer ($V_{FG}$) is greater than said inspiratory volume flow ($V_I$), by integrating a volume flow flowing through said $CO_2$ absorber up to a preset maximum buffer volume and storing it as a $CO_2$-free volume value and by subtracting the value of the $CO_2$-free volume from the integrated volume flow through said $CO_2$ absorber in the next inspiration phase, when said inspiratory volume flow ($V_I$) is greater than said fresh gas volume flow ($V_{FG}$).

4. A method in accordance with claim 1, wherein said computing and control unit is set up to receive and store a maximum quantity of absorbed $CO_2$ which said $CO_2$ absorber can absorb upon an input by an operator, and wherein said computing and control unit initiates an ending of a visual and/or audible signal as soon as the integrated quantity of absorbed $CO_2$ exceeds the stored maximum value.

5. A method in accordance with claim 4, wherein said control unit initiates a visual display of a still remaining absorption capacity of said $CO_2$ absorber on the basis of the integrated quantity of absorbed $CO_2$ and the maximum quantity of absorbed $CO_2$.

6. A method in accordance with claim 5, wherein a residual capacity is displayed as a percentage of the integrated quantity of absorbed $CO_2$ compared to the maximum quantity of absorbed $CO_2$, as a remaining value of the $CO_2$ absorption quantity or as a still remaining residual operating time of said $CO_2$ absorber until the maximum quantity of $CO_2$ is reached in linear extrapolation of a past rate of $CO_2$ absorption.

7. A method in accordance with claim 1, wherein said computing and control unit is connected to an RFID writing and reading device and said $CO_2$ absorber is equipped with an RFID tag, wherein said computing and control unit automatically recognizes a replacement of said $CO_2$ absorber on a basis of the information read from a RFID transponder.

8. A method in accordance with claim 7, wherein said computing and control unit stores a current date as a date of first use in a preset storage location when no date or no valid date is being stored in the preset storage location, or in which said computing and control unit stores Boolean information indicating the use as a flag in the RFID transponder at the preset storage location when said $CO_2$ absorber is put into use.

9. A method in accordance with claim 8, wherein said computing and control unit reads the date of first use or another flag, which was previously stored for this purpose and indicates usage, as a Boolean information from the RFID transponder of said $CO_2$ absorber and provides a visual and/or audible display, which alerts an operator if said $CO_2$ absorber is a previously used $CO_2$ absorber.

10. A method in accordance with claim 7, wherein said computing and control unit automatically resets to zero the integrated quantity of absorbed CO, when replacement of said $CO_2$ absorber is detected, and if an already used $CO_2$ absorber is detected, said computing and control unit prompts the operator to enter the quantity of $CO_2$ already absorbed in said used $CO_2$ absorber for said $CO_2$ absorber as a starting value for the further integration of the absorbed quantity of $CO_2$.

11. A method in accordance with claim 1, wherein said computing and control unit polls an operator if replacement of said $CO_2$ absorber has taken place and, if yes, said computing and control unit resets to zero the integrated quantity of $CO_2$.

12. A respiration method comprising the steps of:
providing a rebreathing system with a fresh gas mixer, a computing and control unit, a respiration drive, a volume flow sensor located in an inspiratory branch, a $CO_2$ absorber located in an expiratory branch, the $CO_2$ absorber providing an output that is combined with an output of said fresh gas mixer and is sent to said inspiratory branch, a breathing gas escape valve and a breathing gas reservoir;
connecting said computing and control unit to said fresh gas mixer, said respiration drive and said volume flow sensor to receive signals and to send control commands;
determining a fresh gas volume discharged from said fresh gas mixer;
determining an inspiration volume flow flowing into the inspiratory branch in said computing and control unit based on flow sensed by said volume flow sensor;
determining a value for a purified rebreathing volume flow added to the inspiration volume flow, from said $CO_2$ absorber, based on a difference of the values of the inspiration volume flow and the fresh gas volume;
determining a measured $CO_2$ concentration value of gas flow entering the $CO_2$ absorber by measuring a $CO_2$ concentration value with a gas sensor connected to the expiratory branch or providing a preset $CO_2$ concentration value of gas flow entering the $CO_2$ absorber to provide an absorber upstream $CO_2$ concentration value;
determining the volume flow entering the absorber from the upstream $CO_2$ concentration value and from the determined purified rebreathing volume flow;
determining a rate of $CO_2$ absorption from a product of the determined volume flow entering the absorber and the upstream $CO_2$ concentration value; and
integrating the determined rate of $CO_2$ absorption over time to provide a determined quantity of the $CO_2$ absorbed in said $CO_2$ absorber.

13. A method in accordance with claim 12, further comprising:
detecting a fresh gas flow phase in which said volume flow from said fresh gas mixer is greater than said inspiratory volume flow as a buffer volume situation;
upon detecting the buffer volume situation, integrating the volume flow flowing through said $CO_2$ absorber, up to a preset maximum buffer volume, during the fresh gas flow phase and storing the integrated volume flow flowing through said $CO_2$ absorber up to a preset maximum buffer volume as a $CO_2$-free volume value; and
subtracting the $CO_2$-free volume value from the integrated volume flow through said $CO_2$ absorber in the next inspiration phase in which said inspiratory volume flow is greater than said fresh gas volume flow.

14. A method in accordance with claim 12, wherein said computing and control unit is set up to receive and store a maximum quantity of absorbed $CO_2$ which said $CO_2$ absorber can absorb upon an input by an operator.

15. A method in accordance with claim 14, wherein said computing and control unit initiates a visual display of a still remaining absorption capacity of said $CO_2$ absorber on the basis of the integrated quantity of absorbed $CO_2$ and the maximum quantity of absorbed $CO_2$.

16. A method in accordance with claim 12, wherein said computing and control unit is connected to an RFID writing and reading device and said $CO_2$ absorber is equipped with an RFID tag, wherein said computing and control unit automatically recognizes the replacement of said $CO_2$ absorber on the basis of the information read from the RFID transponder.

17. A method in accordance with claim 12, wherein the step of determining the volume flow entering the absorber from the upstream $CO_2$ concentration value and from the determined purified rebreathing volume flow is made based on the formula:

$$\dot{V}_{abs}^{in} = \dot{V}_{abs}\left(\frac{100}{100 - Vol.\ \%(CO_2)}\right)$$

where $V_{abs}$ is the volume flow entering the absorber, $V_{abs}$ is the determined purified rebreathing volume flow and Vol. % ($CO_2$) is the upstream $CO_2$ concentration value.

18. A respiration system comprising:
a rebreathing system with a fresh gas mixer, a computing and control unit, a respiration drive, a volume flow sensor located in an inspiratory branch, a $CO_2$ absorber located in an expiratory branch, the $CO_2$ absorber providing an output that is combined with an output of said fresh gas mixer and is sent to said inspiratory branch, a breathing gas escape valve and a breathing gas reservoir, said computing and control unit being connected to said fresh gas mixer, to said respiration drive and to said volume flow sensor to receive signals and to send control commands;
wherein said computing and control unit determines a fresh gas volume discharged from said fresh gas mixer, determines an inspiration volume flow flowing into the inspiratory branch and said computing and control unit determines a value for a purified rebreathing volume flow added to the inspiration volume flow from said $CO_2$ absorber based on a difference of the values of the inspiration volume flow and the fresh gas volume and determines a volume flow entering the $CO_2$ absorber from the value for the purified rebreathing volume flow and a preset or sensed $CO_2$ concentration value of gas flowing into the $CO_2$ absorber and determines a rate of $CO_2$ absorption from the preset or sensed $CO_2$ concentration value and the volume flow entering the $CO_2$ absorber; and
wherein said computing and control unit integrates the determined rate of $CO_2$ absorption over time to determine the quantity of the $CO_2$ absorbed in said $CO_2$ absorber.

19. A system in accordance with claim 18, further comprising:
a radio frequency identification (RFID) reading device, wherein said computing and control unit is connected to said RFID reading device; and
an RFID transponder, said RFID transponder being associated with said $CO_2$ absorber, wherein said computing and control unit automatically recognizes the replacement of said $CO_2$ absorber on the basis of the information read from the RFID transponder.

20. A system in accordance with claim 18, wherein said computing and control unit determines the volume flow entering the absorber from the upstream $CO_2$ concentration value and from the determined purified rebreathing volume flow based on the formula:

$$\dot{V}_{abs}^{in} = \dot{V}_{abs}\left(\frac{100}{100 - Vol.\ \%(CO_2)}\right)$$

where $V_{abs}$ is the volume flow entering the absorber, $V_{abs}$ is the determined purified rebreathing volume flow and Vol. % ($CO_2$) is the upstream $CO_2$ concentration value.

* * * * *